United States Patent
Tunna et al.

(10) Patent No.: US 8,333,573 B2
(45) Date of Patent: Dec. 18, 2012

(54) APPARATUS FOR DETECTING A FLAMMABLE ATMOSPHERE WITHIN A COMPRESSOR, IN PARTICULAR A VACUUM PUMP

(75) Inventors: Clive Marcus Lloyd Tunna, Bolney (GB); Donovan Collins, Bolton (GB); Roland Paul Gregor Kusay, Redhill (GB); Richard Wakefield, Huddersfield (GB)

(73) Assignee: Edwards Limited, Crawley, West Sussex (GB)

( * ) Notice: Subject to any disclaimer, the term of this patent is extended or adjusted under 35 U.S.C. 154(b) by 487 days.

(21) Appl. No.: 12/086,743

(22) PCT Filed: Nov. 9, 2006

(86) PCT No.: PCT/GB2006/050377
§ 371 (c)(1),
(2), (4) Date: Jun. 1, 2010

(87) PCT Pub. No.: WO2007/068969
PCT Pub. Date: Jun. 21, 2007

(65) Prior Publication Data
US 2010/0229626 A1 Sep. 16, 2010

(30) Foreign Application Priority Data

Dec. 15, 2005 (GB) .................................. 0525517.9
Mar. 2, 2006 (GB) .................................. 0604154.5

(51) Int. Cl.
*F04B 49/00* (2006.01)

(52) U.S. Cl. ...................................................... 417/292
(58) Field of Classification Search .................... 417/53, 417/63, 282, 292; 73/23.31, 36, 35.17; 60/39.091–39.094; 436/136, 137, 147, 148, 436/155
See application file for complete search history.

(56) References Cited

U.S. PATENT DOCUMENTS
3,978,877 A 9/1976 Cox
(Continued)

FOREIGN PATENT DOCUMENTS
EP 0 080 184 A1 6/1983
(Continued)

OTHER PUBLICATIONS

Fiumara Annunziata; English language abstract of Publication No. EP0080184 A1; entitled "Apparatus for Controlling the Potential Danger of a Gaseous Mixture Made of Gas and/or Vapor," Stazione Sperimentale Per I Co; Jun. 1, 1983.
(Continued)

*Primary Examiner* — Devon Kramer
*Assistant Examiner* — Amene Bayou

(57) ABSTRACT

Apparatus for detecting a flammable atmosphere within a compressor during operation thereof is provided. The apparatus comprising a test chamber which is selectably connected between the compressor and an exhaust duct of the compressor using isolation device; an ignition device which is located within the test chamber for igniting any flammable fluid mixture present therein; and sensor associated with the test chamber for monitoring a parameter indicative of combustion within the test chamber and for outputting a signal indicative of the parameter to a controller.

37 Claims, 2 Drawing Sheets

U.S. PATENT DOCUMENTS

| | | | |
|---|---|---|---|
| 4,140,004 A | | 2/1979 | Smith et al. |
| 4,220,452 A | | 9/1980 | Bray |
| 4,929,151 A | * | 5/1990 | Long et al. .................... 415/177 |
| 5,591,019 A | | 1/1997 | Brown |
| 6,623,976 B1 | * | 9/2003 | Hale et al. .................... 436/160 |
| 6,715,338 B1 | * | 4/2004 | Hsu ................................ 73/23.2 |
| 2004/0231399 A1 | * | 11/2004 | Gokhfeld .................... 73/23.31 |
| 2005/0019169 A1 | | 1/2005 | Kriehn et al. |
| 2006/0153696 A1 | * | 7/2006 | Ransom et al. ............... 417/228 |

FOREIGN PATENT DOCUMENTS

| | | |
|---|---|---|
| GB | 692712 | 6/1953 |
| GB | 2 013 884 A | 8/1979 |
| WO | WO 2004/036049 A1 | 4/2004 |

OTHER PUBLICATIONS

United Kingdom Search Report of Application No. GB 0525517.9; Claims searched: 1-32; Date of search: May 22, 2006.

PCT Notification of Transmittal of the International Search Report and the Written Opinion of the International Searching Authority, or the Declaration of International Application No. PCT/GB2006/050377; Date of mailing: Jan. 30, 2007.

PCT International Search Report of International Application No. PCT/GB2006/050377; Date of mailing of the International Search Report: Jan. 30, 2007.

PCT Written Opinion of the International Searching Authority of International Application No. PCT/GB2006/050377; Date of mailing: Jan. 30, 2007.

* cited by examiner

APPARATUS FOR DETECTING A FLAMMABLE ATMOSPHERE WITHIN A COMPRESSOR, IN PARTICULAR A VACUUM PUMP

FIELD OF THE INVENTION

The present invention relates to the field of detection of flammable atmospheres, and finds use in one example in the detection of flammable atmospheres within fluid being pumped by a vacuum pump.

BACKGROUND OF THE INVENTION

A vacuum pump may be used in what is commonly referred to as a "house" vacuum system whereby a single vacuum pump or a number of vacuum pumps are used to draw fluid from a number of different enclosures, often serving a number of different laboratories. Consequently, the fluids evacuated by such a house vacuum system can be of indeterminate composition and concentration. Fluids that may not pose any particular hazardous threat when pumped in isolation may, when mixed with similarly innocuous substances, generate hazardous, potentially flammable atmospheres when mixed together inside the vacuum pump.

If the ratio of the flammable fluid mixture to oxidant within the pumped fluid, hereinafter referred to as the concentration of the pumped fluid, lies between certain limits, namely the upper and lower explosion limits (usually expressed as the percentage by volume in air) then combustion will take place if a source of ignition is present.

It is possible to mitigate against a flammable atmosphere being generated within the vacuum pump by introducing quantities of purge gas into the vacuum pump, which dilute the potentially hazardous mixture contained therein. The dilution ensures that the concentration of the pumped fluid remains below the lower explosive limit associated with that particular fluid mixture. If the vacuum pump is evacuating by-products from a known process, an appropriate level of purge gas required may be readily discernable. However, in some circumstances, for example in a house vacuum system, the pumped fluid is of indeterminate composition and consequently significant quantities of purge gas may need to be introduced into the pump to ensure safety requirements are met at all times. The use of purge gas leads to an increased cost of consumables and can be detrimental to the effectiveness of the pumping process. By introducing significant quantities of purge gas into the vacuum pump, the volume of fluid to be transported through the vacuum pump increases significantly. Consequently, a larger capacity pump needs to be provided to accommodate the increased volume of fluid. Disadvantages associated with using a higher capacity pump are increased capital costs, increased volumetric footprint and increased power requirements.

It is therefore desirable to provide a means of detecting a flammable atmosphere, independent of the particular composition of the fluid mixture, to enable techniques for mitigating against the formation of a flammable atmosphere within a device, for example a house vacuum pumping arrangement, to be used more effectively and efficiently. In one example, the extensive use of purge gas may be avoided.

SUMMARY OF THE INVENTION

According to the present invention there is provided apparatus for detecting a flammable atmosphere within a compressor, the apparatus comprising:

a test chamber, connected between the compressor and an exhaust duct of the compressor, for receiving fluid from the exhaust duct;

isolation means for isolating from the compressor and the exhaust duct fluid received by the test chamber;

an ignition device located within the test chamber, for igniting the isolated fluid; and sensing means associated with the test chamber for monitoring a parameter indicative of combustion therein.

By providing apparatus which detects whether a flammable atmosphere is present through physically igniting a sample of the fluid, apparatus capable of detecting any flammable atmosphere, independent of the composition of the flammable fluid mixture to be detected, can be achieved. Consequently, the potential formation of a flammable atmosphere of indeterminate composition, for example, as typically experienced by a house vacuum system, can be mitigated against in an appropriate manner. The need to continuously introduce large quantities of purge gas to dilute the pumped fluid can be removed.

The test chamber may be connected to an inlet of the compressor or to a port located part way along the compressor, between an inlet and an outlet thereof.

The isolation means may be provided by valve means, preferably a pair of positive action valves such as ball valves, one valve being located at an inlet of the test chamber and the second valve being located at an outlet of the test chamber. Alternatively, the apparatus may be configured so that part of the isolation means may be integral with the test chamber. The test chamber may comprise a rotating unit having at least two positions, a first position for enabling fluid communication, through the test chamber, between the exhaust duct and the compressor and a second position for isolating the test chamber from the exhaust duct and the compressor The ignition device may be provided by a glow plug, especially if it is anticipated that the isolated fluid may be readily ignited. Alternatively, in circumstances that the isolated fluid may be less readily ignited, the ignition device may be provided by a high energy ignition source. The ignition source may be configured to deliver a spark having energy in the range of 0.15 Joules to 100 Joules, preferably in the range of 1 Joules to 20 Joules and more preferably in the region of 10 Joules of energy. Control means may be provided for controlling activation of the ignition device. The ignition device may be configured to be activated at predetermined time intervals coinciding with the fluid received by the test chamber being isolated by the isolation means. The ignition device may be configured to be activated repeatedly each time the fluid received by the test chamber is isolated by the isolation means. The ignition device may be configured to be activated for a predetermined duration.

The sensing means may comprise one or more of the group of a pressure sensor, an ionisation sensor, a thermal sensor and an oxygen sensor located within or in fluid communication with the test chamber. The sensing means may also comprise a reference sensor located within or in fluid communication with the exhaust duct of the compressor, for monitoring a reference parameter with which the parameter of the test chamber can be compared.

The present invention also provides apparatus for inhibiting the escalation of a flammable atmosphere within a compressor, comprising:

the aforementioned detection apparatus; and a controller for receiving one or more signals from the sensing means and for controlling inhibition means for inhibiting escalation of any flammable atmosphere detected within the compressor.

The inhibition means may comprise a gas purge system for delivering a purge gas to the compressor upon detection of a flammable atmosphere by the detection apparatus. The location, the quantity and/or the duration of the purge gas delivery may be dependent upon one or more of the following parameters: the magnitude of an increase in monitored pressure; the duration of an increase in monitored pressure; and the number of times a flammable atmosphere is detected within the test chamber. Alternatively or additionally, the inhibition means may be configured to terminate operation of the compressor or isolate the compressor to prevent any further flammable fluid entering the compressor.

The compressor may be a vacuum pump. Accordingly the present invention also provides a pumping arrangement comprising:

a vacuum pump; and the aforementioned apparatus for inhibiting the escalation of a flammable atmosphere within the vacuum pump.

According to the present invention there is also provided a method of detecting a flammable atmosphere within a compressor comprising the following steps:

diverting a sample of fluid from an exhaust duct of the compressor to a test chamber;

isolating the sample of fluid received by the test chamber from the compressor and the exhaust duct;

activating an ignition device within the test chamber; and monitoring a parameter indicative of combustion within the test chamber.

The diverting step may comprise opening isolating means to enable the sample of fluid to pass into the test chamber and the isolating step may comprise closing the isolating means to prevent further passage of fluid therethrough. The activating step may be performed for a first period of time. The ignition device may be repeatedly activated when the test chamber is isolated from the compressor in order to inhibit an accumulation of deposits thereon so that the functionality of the ignition device is maintained.

A signal indicative of the monitored parameter may be outputted from a sensor to a controller for determining whether combustion has occurred within the test chamber, preferably in dependence on a monitored pressure.

The escalation of a flammable atmosphere within the compressor may be inhibited in dependence on the result of the determination by providing a signal to inhibition means for inhibiting escalation of the flammable atmosphere. The inhibition means may be provided by a purge system, whereby purge gas is delivered to the compressor to dilute the fluid located therein.

The ignition device may be periodically cleaned by activating the ignition device for a second period of time, longer than the first period of time required during normal operation. This second period of time may be in the range of 10 seconds to 10 minutes, preferably in the range of 30 seconds to 2 minutes. This cleaning step enables a robust ignition source to be provided which consequently enhances the probability that a flammable atmosphere is detected even after continued normal operation of the compressor.

BRIEF DESCRIPTION OF THE DRAWINGS

The invention is described below in greater detail, by way of example only, with reference to the accompanying drawings, in which.

DETAILED DESCRIPTION OF THE INVENTION

Figure 1:
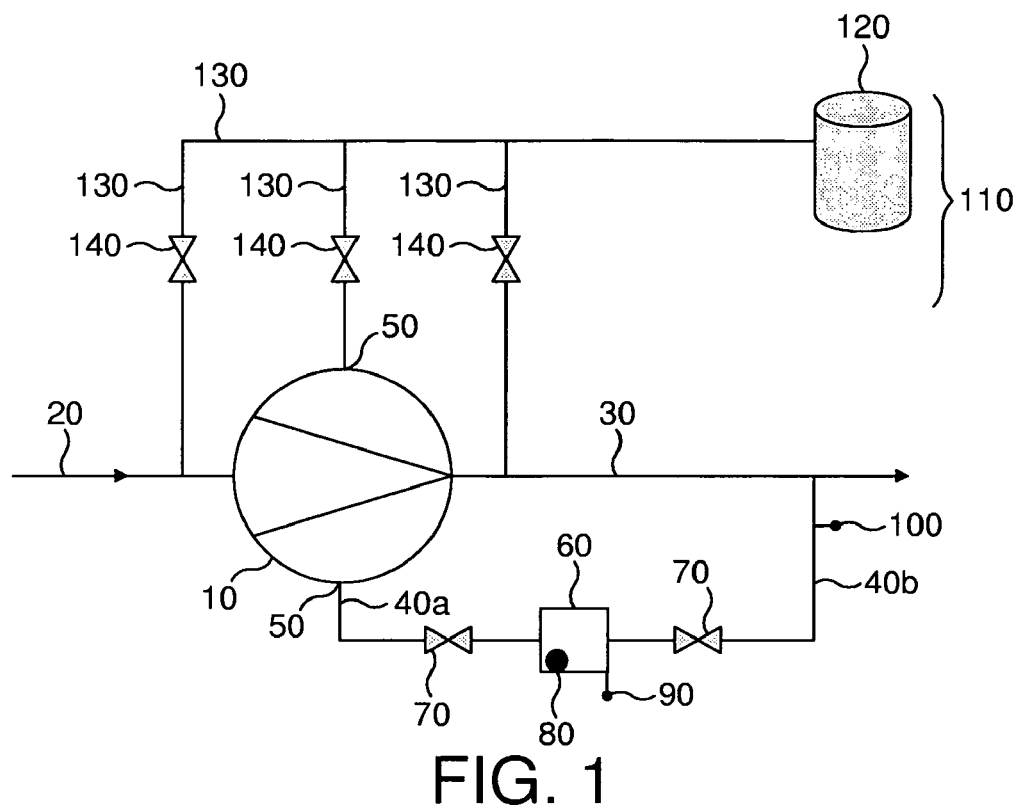
FIG. 1 illustrates apparatus for detecting a flammable atmosphere in a vacuum pump.

Apparatus for detecting the presence of a flammable atmosphere, namely an accumulation of a flammable fluid mixture having a concentration within the combustible limits of that particular fluid mixture, is illustrated in FIG. 1. The apparatus is suitable for use in detecting a flammable atmosphere within any device during operation of that device. However, in this example the apparatus is used to detect a flammable atmosphere within a compressor, which is embodied in this example by a vacuum pump 10. The vacuum pump 10 receives a fluid mixture from an inlet duct 20 and discharges the fluid mixture through exhaust duct 30. The apparatus for detecting the presence of a flammable atmosphere within the pump 10 includes a bypass duct 40 extending between the exhaust duct 30 and the vacuum pump 10. As illustrated, the bypass duct 40 may terminate at one of a number of purge ports 50 provided in a housing of the vacuum pump 10. Alternatively the bypass duct 40 may terminate at an inlet of the vacuum pump 10.

A test chamber 60 is located within the bypass duct 40 and is isolated from the vacuum pump 10 and the exhaust duct 30 by isolation valves 70. Valves 70 are preferably positive action valves, for example gate valves or ball valves.

Figure 2:
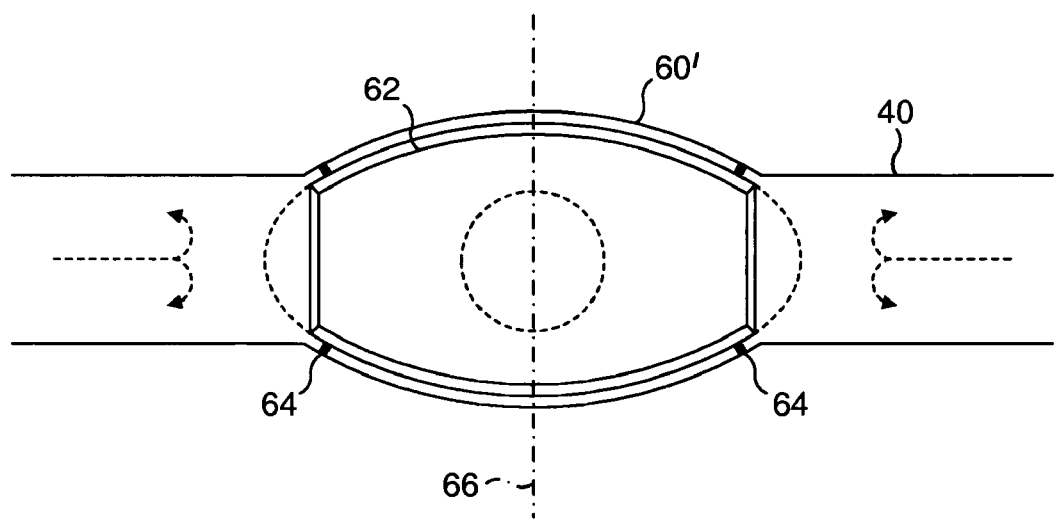
FIG. 2 illustrates an alternative configuration of test chamber that might be implemented in the apparatus of FIG. 1.

FIG. 2 illustrates an alternative test chamber 60' that may be used instead of the test chamber 60 and the positive action valves 70, or just instead of the test chamber 60. The test chamber 60' comprises a rotatable unit 62 located within the bypass duct 40. A sealing element 64 is provided between the bypass duct 40 and the rotating unit 62 to close any potential leak paths therebetween. The rotatable unit 62 can be oriented in line with the bypass duct 40 in a first position as illustrated to permit fluid communication, through the test chamber 60', between the exhaust duct 30 and the vacuum pump 10. However, the rotatable unit 62 can be rotated about axis 66 to a second position (indicated by dashed lines) to isolate the test chamber 60', and thus a sample of fluid, from the exhaust duct 30 and the vacuum pump 10.

An ignition device 80 is located within the test chamber 60; 60'. In some circumstances, for example, when it is anticipated that the fluid mixture to be tested will readily ignite, a glow plug serves as an appropriate ignition device 80. In other circumstances the fluid mixture will be more difficult to ignite and it is therefore necessary to use a high energy ignition source as the ignition device 80, for example if the concentration of the pumped fluid to be sampled is remote from the stoichiometric value and tends towards the explosion limits of the fluid mixture. In practice, very lean mixtures (i.e. those approaching the lower flammability limit of the mixture) are most likely to be experienced during normal operation of the compressor, and although such mixtures are flammable they do not readily ignite. If such lean mixtures can be forced to ignite so that they can be detected early, a build up of a flammable atmosphere having a composition closer to the stoichiometric value, and therefore potentially resulting in a more energetic deflagration, can be avoided. The high energy ignition source is capable of delivering a spark having an energy value of between 0.15 and 100 Joules. Preferably the ignition source is able to deliver a spark having an energy value of between 1 and 20 Joules, more preferably around 10 Joules. Thermally, the spark preferably reaches a temperature in the region of 10,000 Kelvin. The spark may be activated for a duration in the range of 1 μs to 10 seconds but is preferably activated for 1 ms to 3 ms during normal operation.

When some fluid mixtures are ignited, for example particularly rich mixtures (i.e. those having a concentration of the pumped fluid tending towards the upper explosive limit) high levels of particulate by-products such as soot can be produced. The high energy ignition source is typically prone to an accumulation of these by-products. If these by-products were to build up significantly on surfaces of the ignition source the performance of the ignition source would be affected detrimentally. Under these conditions it is beneficial to repeatedly activate the ignition source until the air borne soot particles have settled. In so doing the active components, namely electrodes and surfaces of insulators in the vicinity of the electrodes, of the ignition source remain substantially deposit free and efficient operation of the ignition source is maintained.

Soot or other deposits may form on the electrodes of the spark plug, and the build up of deposits may lead to the gap between the electrodes being bridged. Alternatively, the nature of the fluid mixture may be such that the surfaces of the electrodes become coated with a material. In either case, contamination of the electrodes may prevent the spark plug from generating a spark. Under such circumstances, a cleaning cycle of operation of the spark plug may be initiated. The cleaning cycle involves generating a spark of significantly longer duration than that required by the normal operational cycle. For example the electrodes of the spark plug may be activated for a duration in the range of five seconds to ten minutes, preferably in the range of 30 seconds to two minutes. Whilst a spark will not initially be generated, the power delivered by the electrodes is sufficient to burn away any deposits formed on their surfaces. In other words, cleaning of the electrodes' surfaces is effected by activating the electrodes for this longer duration. Once the deposits have burned away the electrodes will function in the normal operational mode of the spark plug.

The cleaning cycle is preferably carried out in situ without removing the ignition device from its normal operational position. However, especially in the event that the electrodes have become severely contaminated, it may be preferable to remove the spark plug from the apparatus and activate the spark plug's cleaning cycle remotely therefrom. A second spark plug can be positioned in the test chamber 60; 60' to ensure continued operation of the apparatus.

A sensor 90 is associated with the test chamber 60; 60' to monitor a parameter indicative of the presence of combustion therein. In this example a pressure sensor 90 is used, however, a rapid response thermal sensor, an oxygen sensor or an ionisation sensor may also be implemented either alone or in combination with one of the other types of sensor. A second sensor 100 may be used as a reference sensor to help to eliminate background trends or noise in the monitored parameter data. Alternatively, a similar comparison may be achieved by using a pressure monitored by sensor 90 prior to activation of the ignition source as a reference pressure.

A purge system 110 is illustrated in FIG. 1, whereby a source of purge gas 120 is provided in selectable fluid communication with the vacuum pump 10. The purge gas system 110 includes a number of purge lines 130, each provided with a respective variable valve 140, so that purge gas can be delivered at different locations along the vacuum pump 10. FIG. 1 illustrates purge ports 50 respectively located at an inlet of the vacuum pump, part way along a housing of the vacuum pump and at an exhaust of the vacuum pump 10.

In operation, fluid is transported through the vacuum pump 10 and exits therefrom via the exhaust duct 30. Valves 70 are opened to thereby present a clear bypass duct 40 extending between the vacuum pump 10 and the exhaust duct 30 through the test chamber 60; 60'. The bypass duct 40 joins the vacuum pump 10 at a purge port 50 located upstream of the exhaust, but as described above it could be located at the inlet of the vacuum pump 10. The pressure within a portion of the bypass duct 40a adjacent the vacuum pump 10 is, therefore, lower than that within a portion of the bypass duct 40b adjacent the exhaust duct 30. Consequently, the pressure gradient experienced by the bypass duct 40 enables a sample of the fluid to be diverted from the exhaust duct 30 along the portion of the bypass duct 40b and into the test chamber 60; 60'. After a period of time sufficient to substantially replace the fluid within the test chamber 60, the valves 70 (or rotatable unit 62) are closed to isolate the sample of fluid retained within the test chamber 60; 60'. This time period may be of predetermined duration or it may be dependent on the current speed of the vacuum pump 10.

The closure of the valves 70 serves to inhibit propagation of any flame front from the test chamber 60, 60'. Once the valves have been closed the ignition device 80 is activated to attempt to initiate combustion of the isolated fluid within the test chamber 60; 60'. If the sample of fluid contained in the test chamber 60; 60' is flammable and has a concentration between the lower and upper explosive limits, combustion occurs. If the sample of fluid is either not flammable by nature or is of a flammable type but the concentration of the pumped fluid that outside the explosive limits, combustion does not occur. Sensor 90 monitors at least one of a number of parameters that indicate whether a combustion event has occurred or not, for example pressure or temperature. The valves 70 are then opened, the contents of the test chamber 60; 60' are transported to the port 50 of the vacuum pump 10 by virtue of the aforementioned pressure gradient, and a fresh sample of fluid to be tested enters the test chamber 60; 60'.

Figure 3:
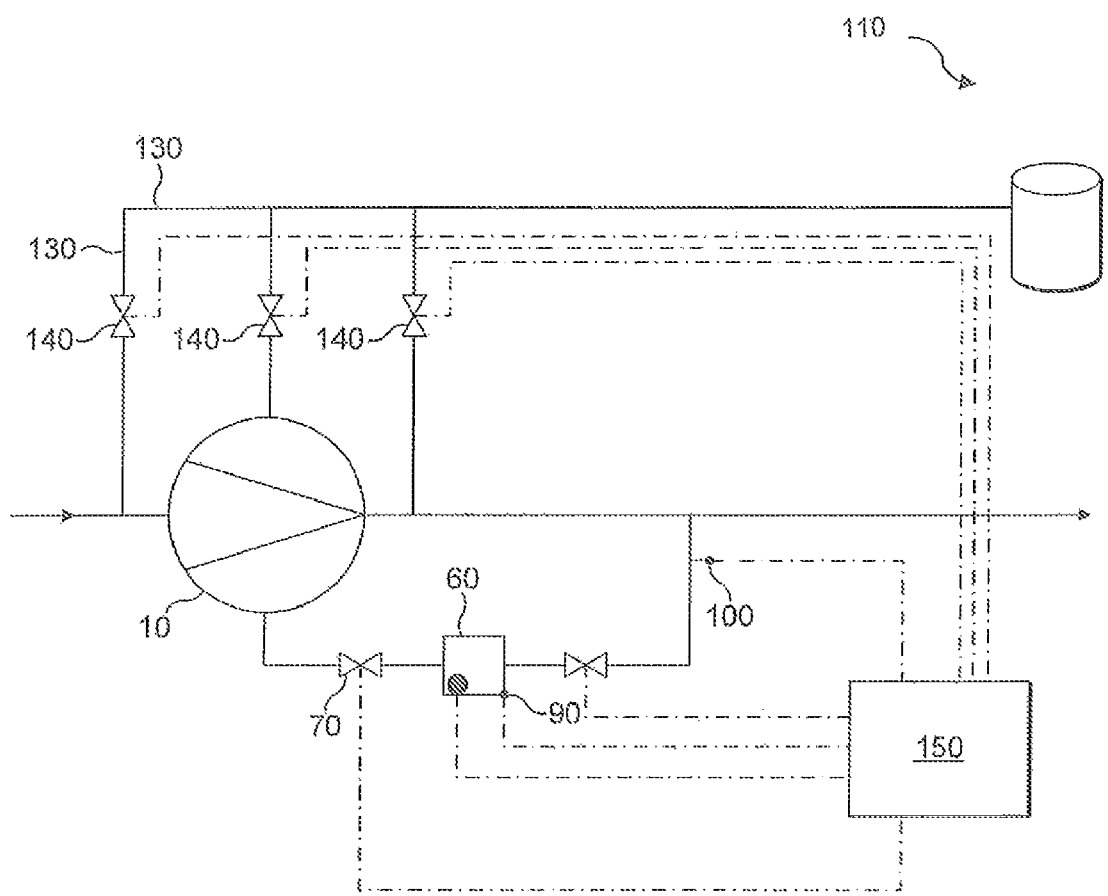
FIG. 3 illustrates the apparatus of FIG. 1 together with a controller for controlling the supply of purge gas to the pump.

Determination of whether a combustion event has occurred within the test chamber 60; 60' is carried out by a controller 150, illustrated in FIG. 3. Signals indicative of the monitored parameter are received from the sensor 90 by the controller 150. The sensor 90 may continuously monitor the parameter to build up a historical trace of the data. Alternatively the sensor 90 may monitor whether a threshold value is exceeded and send a signal to the controller 150 when this value has been exceeded. In either circumstance, as mentioned above a second sensor 100 may be used to monitor the same parameter outside the test chamber 60; 60'. By providing the controller 150 with reference data from the second sensor 100, global changes in the monitored parameter can be separated from the changes monitored locally within the test chamber by sensor 90. The accuracy of the determination of the presence of combustion can, therefore, be enhanced. The controller 150 can also be used to control the actuation of valves 70 (and/or rotatable unit 62) to further increase automation of the testing process.

As indicated in FIG. 3, the controller 150 controls the actuation of the variable valves 140 that, in turn, control the flow of purge gas to be delivered to the vacuum pump 10 through purge ports 50. Upon detection of a combustion event in the test chamber 60; 60', it can be assumed that at least some of the fluid being transported through the vacuum pump 10 is flammable and of a concentration that may combust if an ignition source were to be provided, leading to an explosion within the vacuum pump 10. An ignition source can be generated within any device having moving metal components. If any of those components were to come into contact with one another a spark may be initiated. Contact may occur in the event that the condition of the device, for example a compressor such as a vacuum pump, has deteriorated through extensive use causing the components to become misaligned and thereby increasing the likelihood of clashing. Even if there is no potential for the clashing of components to generate a spark, the thermal environment within the pump could be elevated to increase the risk that auto-ignition may occur. Such an elevated temperature may be experienced in circumstances in which the vacuum pump is heated in order to inhibit condensation of the pumped fluid. The delivery of purge gas mitigates against the formation and subsequent escalation of a significant volume of combustible fluid in the pump 10 by diluting the atmosphere therein.

Alternative methods of inhibiting the escalation of a flammable atmosphere and avoiding an explosion would be to discontinue the flow of flammable fluid into the vacuum pump 10, again preventing the accumulation of the atmosphere and terminating the operation of the vacuum pump 10 to prevent further fluid being drawn into the vacuum pump, and to remove the potential ignition source.

Introduction of purge gas is the preferred option as continuation of operation of the vacuum pump 10 may be achieved. Delivery of purge gas may be initiated by the controller 150 and then continued for a predetermined duration. At the end of this duration, delivery may be terminated and the sampling continued in order to confirm that the flammable atmosphere has dissipated. Sampling may continue throughout delivery of the purge gas in order to monitor the concentration of pumped fluid to determine whether sufficient purge gas is being delivered. Given the nature of a house vacuum system, it is likely that any flammable atmosphere will be generated in a sporadic manner, and so it may be more efficient to provide purge gas during periods of accumulation rather than on a continued basis.

In another embodiment, data relating to the number, duration and magnitude of any combustion events or explosions that occur within the test chamber 60; 60' are maintained by the controller 150. The controller 150 may use the aforementioned data to determine whether delivery of purge gas to the vacuum pump 10 is required in order to dilute a potentially flammable atmosphere. Further, the data may be used to determine the duration and flow rate of the delivery, and to which part of the vacuum pump 10 delivery of purge gas would be most appropriate. The variable valves 140 are then controlled accordingly. If purge gas is to be introduced at the inlet of the vacuum pump 10 the flow rate thereof is preferably low in order to avoid disruption of the inlet flow. Alternatively, in the event that purge gas is introduced either at the exhaust of the vacuum pump 10 or part way along the pump between the inlet and the outlet, an increased quantity of purge gas can be delivered to the pump without affecting the inlet flow and pressure and hence the capacity of the vacuum pump 10.

If the addition of purge gas is insufficient to alleviate the accumulation of flammable fluid within the vacuum pump 10 it may become necessary to initiate shut down or isolation of the vacuum pump 10 in order to prevent the occurrence of a potential explosion therein.

In the event that the distance between the test chamber 60; 60' and the vacuum pump 10 is significant, the sample of fluid within the test chamber 60; 60' may be significantly cooler than the fluid mixture within the vacuum pump 10. Consequently, the sample may not be representative of the fluid mixture within the vacuum pump 10, particularly if the fluid mixture in question comprises condensable materials as the flammable properties of the fluid mixture may be altered. It is, therefore, desirable to thermally control the exhaust duct 30 to maintain the fluid mixture at a substantially constant temperature to prevent formation of condensates that would not be present within the vacuum pump 10. Thermal control may be achieved by providing a heated exhaust duct 30, a heated bypass duct 40 and/or a heated test chamber 60; 60'.

While the foregoing description and drawings represent the preferred embodiments of the present invention, it will be apparent to those skilled in the art that various changes and modifications may be made therein without departing from the true spirit and scope of the present invention.

We claim:

1. Apparatus for detecting a flammable atmosphere within a compressor during operation thereof, the apparatus comprising:
    a test chamber for receiving fluid, wherein the test chamber is connected to a bypass line between the compressor and an exhaust duct of the compressor or connected to a port of the compressor located between an inlet of the compressor and the exhaust duct of the compressor
    isolation means for isolating the fluid received by the test chamber
    an ignition device located within the test chamber, for igniting the isolated fluid; and
    sensing means associated with the test chamber for monitoring a parameter indicative of combustion therein.

2. Apparatus according to claim 1 wherein the isolation means comprise valve means.

3. Apparatus according to claim 2 wherein the valve means comprise a pair of positive action valves, one located at an inlet of the test chamber and the second located at an outlet of the test chamber.

4. Apparatus according to claim 3 wherein the positive action valves are provided by ball valves.

5. Apparatus according to claim 1 wherein at least part of the isolation means is integral with the test chamber and comprises a rotating unit having a first position for enabling fluid communication through the test chamber, and a second position for isolating the test chamber from the exhaust duct and the compressor.

6. Apparatus according to claim 1 wherein the ignition device is provided by a glow plug.

7. Apparatus according to claim 1 wherein the ignition device is provided by a high energy ignition source.

8. Apparatus according to claim 7 wherein the ignition source is configured to deliver a spark having energy in the range of 0.15 Joules to 100 Joules.

9. Apparatus according to claim 8 wherein the ignition source is configured to deliver a spark having energy in the range of 1 Joules to 20 Joules.

10. Apparatus according to claim 9 wherein the ignition source is configured to deliver a spark having about 10 Joules of energy.

11. Apparatus according to claim 7 wherein the ignition source is configured to deliver a spark for a duration in the range of 1 µs to 10 seconds.

12. Apparatus according to claim 11 wherein the ignition source is configured to deliver a spark for a duration in the range of 1 ms to 3 ms.

13. Apparatus according to claim 1 comprising control means for controlling activation of the ignition device.

14. Apparatus according to claim 1 wherein the ignition device is configured to be activated at predetermined time intervals.

15. Apparatus according to claim 1 wherein the ignition device is configured to be repeatedly activated.

16. Apparatus according to claim 1 wherein the sensing means comprises a pressure sensor located within or in fluid communication with the test chamber.

17. Apparatus according to claim 1 wherein the sensing means comprises at least one of an ionisation sensor, a thermal sensor and an oxygen sensor located within or in fluid communication with the test chamber.

18. Apparatus according to claim 16 wherein the sensing means comprises a reference sensor located within or in fluid communication with either the exhaust duct of the compressor or said port of the compressor, for monitoring a reference parameter comparable to said parameter indicative of combustion in the test chamber.

19. Apparatus for inhibiting an escalation of a flammable atmosphere within a compressor during operation thereof, comprising:
   a test chamber for receiving fluid, wherein the test chamber is connected to a bypass line between the compressor and an exhaust duct of the compressor
   isolation means for isolating the fluid received by the test chamber from the compressor, and the exhaust duct
   an ignition device located within the test chamber, for igniting the isolated fluid; and
   sensing means associated with the test chamber for monitoring a parameter indicative of combustion therein; and
   a controller for receiving one or more signals from the sensing means and for controlling an inhibition means, wherein the inhibition means inhibits escalation of any flammable atmosphere within the compressor.

20. Apparatus according to claim 19 wherein the inhibition means comprises a gas purge system for delivering a purge gas to the compressor upon detection of a flammable atmosphere.

21. Apparatus according to claim 20 wherein a quantity or duration of the purge gas delivery is dependent upon an increase in the monitored parameter, a duration of an increase in the monitored parameter or the number of times a flammable atmosphere is detected.

22. Apparatus according to claim 19 wherein the inhibition means is configured to isolate and/or terminate operation of the compressor.

23. Apparatus according to claim 1 wherein the compressor is a vacuum pump.

24. A pumping arrangement comprising:
   a vacuum pump; and
   apparatus for inhibiting the escalation of a flammable atmosphere within the vacuum pump comprising:
      a test chamber for receiving fluid, wherein the test chamber is connected to a bypass line between the vacuum pump and an exhaust duct of the vacuum pump
      a valve for isolating from the vacuum pump and the exhaust duct fluid received by the test chamber;
      an ignition device located within the test chamber, for igniting the isolated fluid; and
      a sensor associated with the test chamber for monitoring a parameter indicative of combustion therein; and
      a controller for receiving one or more signals from the sensing means and for controlling an inhibition means, wherein the inhibition means inhibits escalation of any flammable atmosphere within the compressor.

25. The pumping arrangement according to claim 24, wherein the exhaust duct and/or the test chamber comprise heating means for inhibiting condensation of a fluid contained therein.

26. A method of detecting a flammable atmosphere within a compressor during operation thereof comprising the following steps:
   diverting a sample of fluid from the compressor via a bypass line connecting the compressor and an exhaust duct of the compressor, wherein the bypass line is connected to a test chamber
   isolating the sample of fluid received by the test chamber from the compressor and the exhaust duct;
   activating an ignition device within the test chamber; and
   monitoring a parameter within the test chamber.

27. The method according to claim 26 wherein the diverting step comprises opening isolating means to enable the sample of fluid to pass into the test chamber and the isolating step comprises closing the isolating means to prevent further passage of fluid therethrough.

28. The method according to claim 26 wherein the activating step comprises repeatedly activating the ignition device to inhibit an accumulation of deposits inside the test chamber.

29. The method according to claim 26 wherein the monitored parameter is pressure.

30. The method according to claim 26 comprising the steps of:
   outputting a signal indicative of the monitored parameter from a sensor to a controller; and
   determining whether combustion occurs within the test chamber in dependence on the monitored parameter.

31. The method of claim 26 comprising:
   providing a signal to an inhibition means for inhibiting escalation of the flammable atmosphere.

32. The method according to claim 31 wherein the inhibition means is provided by a purge system, the method comprising the step of delivering purge gas to the compressor to dilute the fluid located therein.

33. The method according to claim 26 wherein the ignition device is activated for a first period of time to ignite fluid within the chamber, and is periodically cleaned by activation for a second period of time longer than the first period of time.

34. The method according to claim 33 wherein the first period of time is in the range of 1 μs to 10 seconds.

35. The method according to claim 34 wherein the first period of time is in the range of 1 ms to 3 ms.

36. The method according to claim 33 wherein the second period of time is in the range of 5 seconds to 10 minutes.

37. The method according to claim 36 wherein the second period of time is in the range of 30 seconds to 2 minutes.

* * * * *